United States Patent [19]

Luman

[11] Patent Number: 5,002,578
[45] Date of Patent: Mar. 26, 1991

[54] MODULAR HIP STEM PROSTHESIS APPARATUS AND METHOD
[75] Inventor: David P. Luman, Ogden, Utah
[73] Assignee: Venus Corporation, Ogden, Utah
[21] Appl. No.: 518,990
[22] Filed: May 4, 1990
[51] Int. Cl.$^5$ ............................................. A61F 2/36
[52] U.S. Cl. .......................................... 623/23; 623/18
[58] Field of Search ................... 623/23, 22, 18, 16

[56] References Cited
U.S. PATENT DOCUMENTS

| 3,067,740 | 12/1962 | Haboush | 623/22 X |
| 3,820,167 | 6/1974 | Sivash | 623/22 |
| 3,987,499 | 10/1976 | Scharbach et al. | 623/22 X |
| 4,051,559 | 10/1977 | Pifferi | 623/22 |
| 4,790,852 | 12/1988 | Noiles | 623/23 X |
| 4,822,370 | 4/1989 | Schelhas | 623/23 |
| 4,846,839 | 7/1989 | Noiles | 623/18 |

Primary Examiner—Ronald Frinks
Attorney, Agent, or Firm—J. Winslow Young

[57] ABSTRACT

A modular hip stem prosthesis including a hip stem with an integral, enlarged shoulder and a neck section mountable to the hip stem. The integral, enlarged shoulder is designed to closely conform to the metaphyseal region to securely mount the hip stem in the end of the femur. The enlarged, shoulder portion of the hip stem is also selectively configured to be fabricated as a separate element so as to allow one of a plurality of distal stems to be mounted to the enlarged shoulder to create the hip stem. The neck section readily adapts the hip stem prosthesis for repair and replacement of the components of the total hip replacement without requiring replacement of the hip stem.

11 Claims, 4 Drawing Sheets

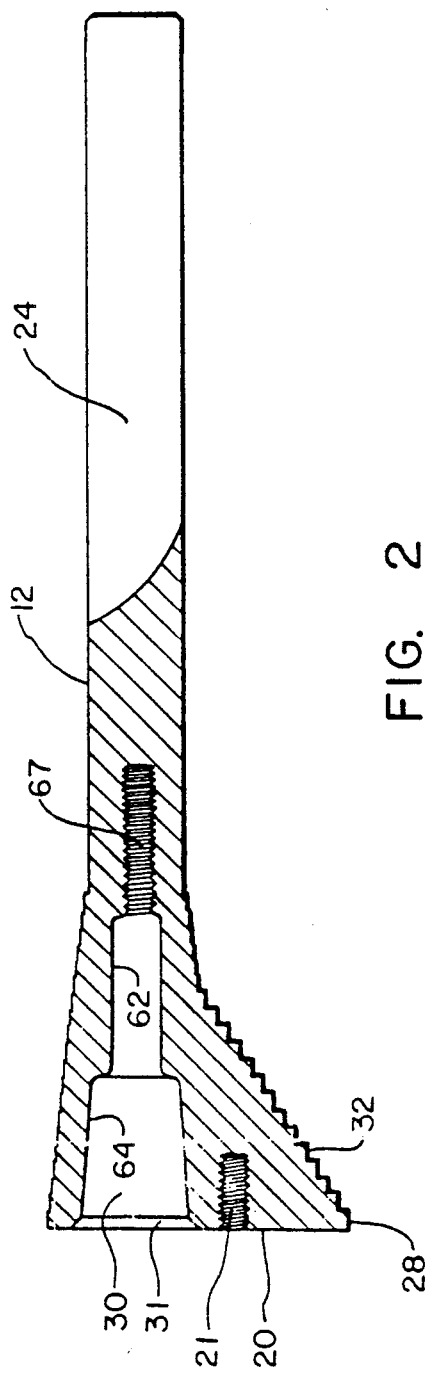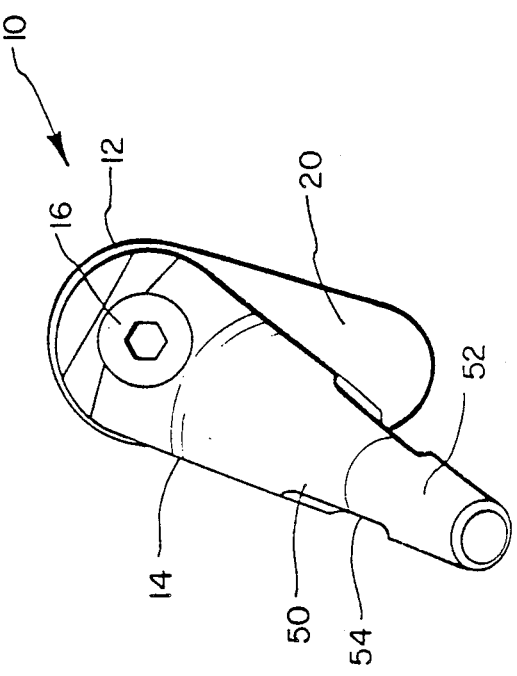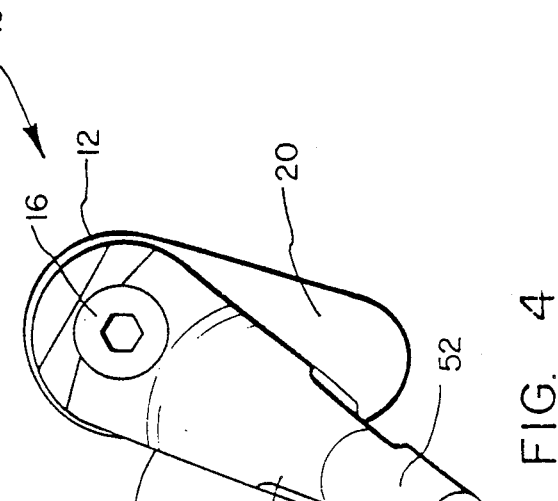

MODULAR HIP STEM PROSTHESIS APPARATUS AND METHOD

BACKGROUND

1. Field of the Invention

This invention relates to prosthesis apparatus and methods for a total hip replacement and, more particularly to a novel, modular hip stem prosthesis apparatus and method whereby the hip stem is provided as a modular system having interchangeable stem elements and mating neck elements all of which are adapted to be releasably interconnected to provide a hip stem prosthesis that is selectively configured to conform to the specific anatomical conditions encountered during the surgical procedure.

2. The Prior Art

Numerous devices have been developed as total hip replacements with the basic feature being a system for replacing the natural ball and socket of the hip joint with an artificial ball and socket arrangement. One device referred to in the art as the Sivash prosthesis (Sivash, U.S. Pat. No. 3,820,167, Artificial Hip Joint) was developed through work that began around 1956 at the Central institute for Orthopedics and Traumatology, Moscow, Russia. This work included selection of certain metals and alloys for the device with the major emphasis being on the design of a constrained socket. According to one report the Sivash prosthesis never received major clinical or market success in part due to the difficulty of the surgical procedure and the positioning of this constrained device. In any event, the Sivash prosthesis made contributions toward the femoral stem in the area of a titanium alloy for the femoral stem with a chrome cobalt for the head articulation and titanium alloy proximal sleeves for enhanced collar/calcar contact. The original Sivash femoral stem was a round, tapered peg which led to a number of noncemented failures due to rotation of the stem in the femur. The result was that a number of these prostheses were cemented after the FDA approved the use of bone cement.

Rotation in the femoral canal remained a problem in cementless arthroplasty until the development of the fluted stem which involves a plurality of longitudinal flutes being incorporated into the distal part of the stem. Bending stiffness of the stem was reduced by adding a distal coronal slot thereby insuring minimal distal-load transfer. The coronal slot also resiliently urges the longitudinal flutes outwardly into engagement with the inner walls of the femoral canal adjacent the distal end.

Fixation of the hip stem prosthesis in the proximal femoral area has been the focus of a series of sleeves designed to be releasably mounted to the proximal end of the stem. Various configurations of this sleeve have been proposed and range among (a) cylindrical, (b) externally threaded sleeves, and (c) femoral sleeves having an exterior self-tapping, conical bone screw thread for achieving immediate, secure, mechanical fixation of the stem in the proximal femur. In place of the threaded configurations, other sleeves are configured as porous coated cones to encourage tissue ingrowth to the prosthesis. The porous coating is achieved by sintering a layer of titanium beads to the substrate. These cones are provided with or without a series of steps or ridges formed transversely around the cone.

The sleeve/stem combination was designed to provide the surgeon with a plurality of sleeve sizes and configurations received in mating relationship with a stem selected from a plurality of stem configurations. Conventionally, the mating surface is a taper having about a three degree tapered section so that when joined together the sleeve will not rotate relative to the stem.

Examples of such sleeve and stem combinations are found in U.S. Pat. Nos. 4,790,852 and 4,846,839. In each of these patents and in all other known hip stem prostheses, the sleeve is interchangeably mounted to the proximal end of the stem. The remainder of the proximal end of the stem is formed into an integral neck portion which incorporates various configurations to adapt the particular stem for a specific implant application. Accordingly, while the sleeve is interchangeable, each stem is restricted to a particular neck configuration. Further, greater diversity is encountered in the different neck configurations than between the distal portion of the particular stem and the sleeve.

In view of the foregoing it would be a significant advancement in the art to provide a hip stem and a mating neck assembly removably mounted to the stem, the stem including an integral, graduated collar system for mounting the stem in the femoral cavity. It would also be advantageous to provide a modular hip stem whereby various lengths and diameters of distal stem can be secured to the collar system to provide for a more uniform fit of the hip stem prosthesis in the femoral cavity. Another advancement would be to provide a mating neck assembly that includes a plurality of configurations and is removably mated to the stem. An even further advancement would be to provide for the replacement of the neck portion of the hip stem without necessarily also removing and replacing the distal stem portion of the hip stem. Such a novel apparatus and method is disclosed and claimed herein.

BRIEF SUMMARY AND OBJECTS OF THE INVENTION

This invention relates to a novel hip stem apparatus and method whereby the hip stem includes a separable, mating neck section and a separable, mating distal stem portion. The neck section is selected from a plurality of profiles that may be selectively chosen to fit the particular requirements encountered by the surgeon during surgery. The distal stem is fabricated with an integral, graduated collar section which is configured to securely support and engage the proximal end of the stem in the proximal end of the femoral cavity. The distal portion of the distal stem is provided with a series of predetermined lengths and diameters and may also be selectively and removably mounted to the collar section.

It is, therefore, a primary object of this invention to provide improvements in hip stem prostheses apparatus.

Another object of this invention is to provide improvements in the method of providing a hip stem prosthesis.

Another object of this invention is to provide a novel hip stem prosthesis wherein the stem portion and the neck portion are fabricated as separate assemblies, each having a plurality of configurations and being adapted to be matingly engaged into the hip stem prosthesis.

Another object of this invention is to provide the hip stem with an integral, diametrally enlarged collar section having a tapered, eccentric profile.

Another object of this invention is to provide the distal portion of the hip stem prosthesis as a modular system whereby distal portions of different lengths and diameters can be interchangeably mounted to the collar section.

These and other objects and features of the present invention will become more readily apparent from the following description in which preferred and other embodiments of the invention have been set forth in conjunction with the accompanying drawing and appended claims.

BRIEF DESCRIPTION OF THE DRAWING

FIG. 2 is a cross sectional view of the stem portion of the first preferred embodiment of the hip stem prosthesis of this invention taken along lines 2—2 of FIG. 1;

FIG. 3 is a cross sectional view of the neck portion of the first preferred embodiment of the hip stem prosthesis of this invention taken along lines 3—3 of FIG. 1;

FIG. 4 is an end view of the first preferred embodiment of the hip stem prosthesis of this invention shown in the assembled configuration with the neck portion angularly offset from the longitudinal axis of the collar section of the stem portion of the hip stem prosthesis to illustrate the range of angular offset available through this novel invention.

DETAILED DESCRIPTION

Figure 1:
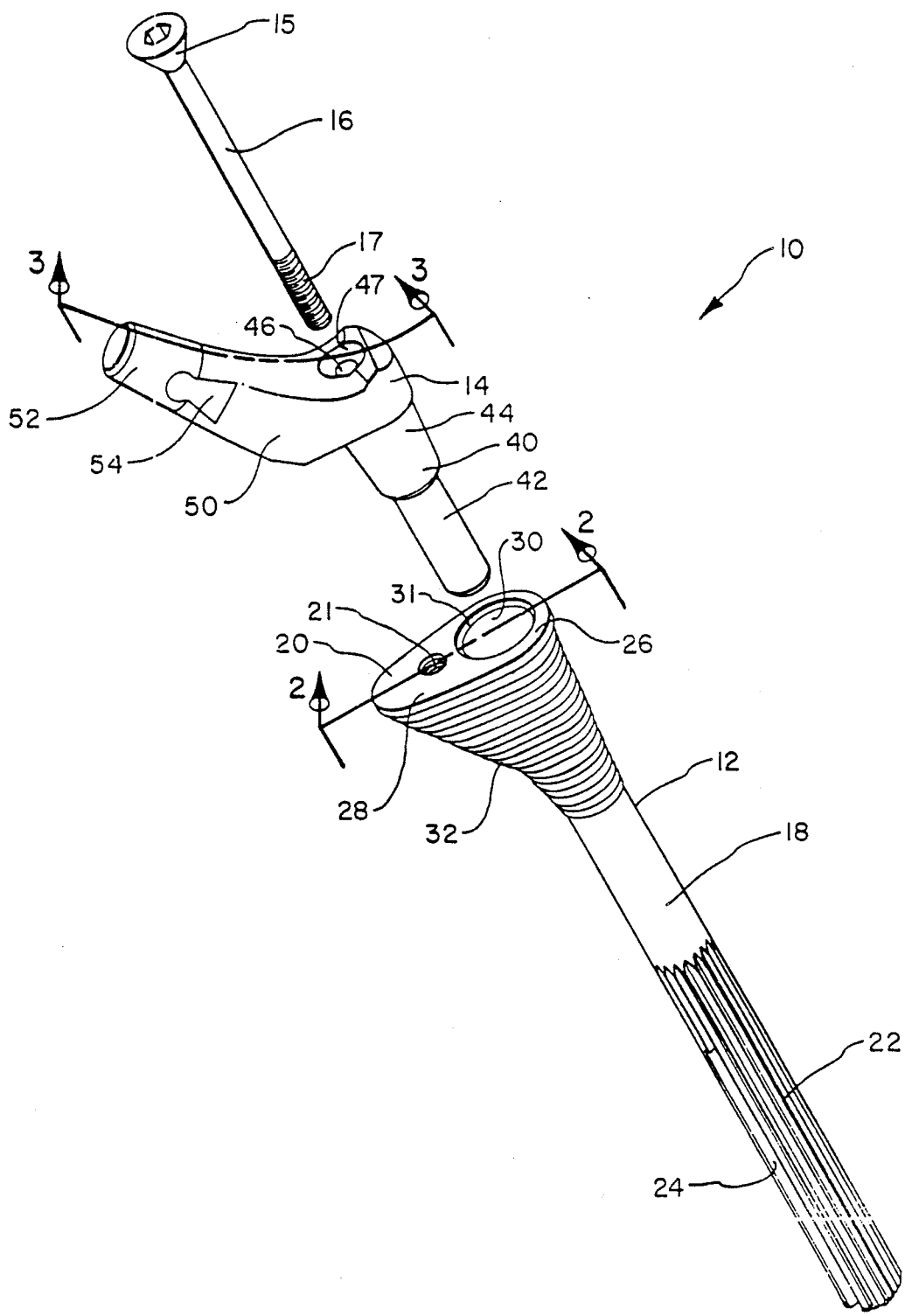
FIG. 1 is an exploded, perspective view of a first preferred embodiment of the novel hip stem prosthesis of this invention.

The invention is best understood by reference to the drawing wherein like parts are designated by like numerals throughout in conjunction with the following description.

GENERAL DISCUSSION

Obtaining a precision fit of the hip stem prosthesis in the femoral canal that has been prepared by the surgeon is one of the major difficulties encountered in implanting a total hip replacement prosthesis. The profile of the femoral canal is dictated to a large degree by the characteristics of both the femur itself and the shape of the top of the medullary shaft. Importantly, great care is taken to obtain the best fit possible in order to provide optimal force distribution between the total hip replacement prosthesis and the femur. The surgeon prepares the femur to receive the hip stem prosthesis by simple straight reaming which defines the length and diameter of the stem prosthesis. The next step is to match the internal contour of the cortical bone with the size and shape of the collar.

A recent advancement in the hip stem prosthesis has been to provide a demountable, truncated collar or sleeve that is adapted to be mounted on the hip stem in press fit relationship adjacent the proximal end of the hip stem prosthesis. The purpose of the sleeve is to closely approximate the triangular flare routed from the top of the medullary shaft. This triangular flare is routed with a calcar miller mounted at an angular offset to a pilot shaft that passes into the femoral canal that has been drilled previously. The size and angular orientation of the calcar miller is predetermined by the surgeon during the surgical procedure as a function of the size and shape of the proximal medial femur. The calcar cutter is pushed downwardly until the cut into the proximal medial femur closely approaches the cortical bone.

One major challenge facing the surgeon is inhibiting hip dislocation. For instance, in a congenital hip dislocation the upper part of the bone is twisted, usually anteriorly. Placement of a regular, uncemented hip prosthesis into the bone under these conditions will result in dislocation of the prosthesis because the prosthesis will be positioned too far anteriorly. This problem is addressed by having the sleeve and stem lock together with a friction taper known in the art as the Morse taper. Angle choice between the stem and the sleeve is done at the time of surgery by the surgeon looking along the leg, holding the tibia horizontally to the floor. The desired orientation is for the hip to be facing about fifteen degrees to the front so that alignment is not made with the femur but on the tibia.

The first step involves the reaming of the femoral canal. The most crucial aspect of reaming is ensuring that the isthmus is reamed in a neutral varus/valgus position since this determines the position of the femoral implant. Starting with the smallest reamer the surgeon then moves up to the larger sizes. The length and diameter of the final straight distal reamer should be recorded, since this measurement dictates the length and diameter of the distal stem.

Next, the size of proximal cone to be cut to receive the collar is selected and prepared. The size of the collar is directly related to the size of the proximal stem diameter. As in the femoral canal, the surgeon progresses from the smallest proximal conical reamer to the largest in the series. The lateral aspect of the trochanter will be invaded, as will the posterior area of the femoral neck.

Femoral neck length is established by matching the superior level of the greater trochanter with appropriate gauge markings on the proximal conical reamer, which correspond to the available neck lengths of each stem. A transverse osteotomy is then performed perpendicular to the femoral shaft axis, slightly above the level of the proximal end of the conical reamer flutes. After the osteotomy, the proximal conical reamer is removed. Next, the triangular flare of the sleeve is prepared. Using a calcar miller fitted with an appropriately sized distal pilot shaft, the surgeon machines the proximal medial part of the femur down to cortical bone, taking care to align the miller for maximum containment in the triangular flare. After cutting, the miller is removed.

Advantageously, the present invention accommodates secure implantation of the hip stem prior to selecting the appropriate neck portion of the hip stem prosthesis. The novel apparatus and method of this invention allows the surgeon to affix the acetabulum prosthesis of the cotyloid cavity prior to interconnecting the hip ball to the curved neck which is then joined to the proximal end of the hip stem. This novel feature greatly simplifies initial implantation and subsequent replacement of the various parts subject to wear.

For example, one of the primary difficulties in hip surgery is conversion or retrievability of implants. Conversion is the need to adjust, replace, or reposition some components. For example, to increase hip stability it may be necessary to dial a polyethylene offset into acetabular cup after the femoral head has been reduced. Also, an implant inserted in a young person may fail in time. If the fixation does not loosen or the implant break, then the plastic bearing will eventually wear out in any case.

Importantly, revision should be accomplished with minimal bone destruction. Historically, revision has required the complete removal of the hip stem even though the hip stem, per se, has not failed. Removal of the hip stem is even facilitated by reducing the chances of distal osteointegration, the direct apposition of the bone to the distal stem, by providing a distal portion of the stem that is highly polished.

The present invention provides a novel, modular hip replacement prosthesis which is not only easier to implant but is also much easier to work with during revision since only the failed or worn components need to be replaced.

THE PREFERRED EMBODIMENTS

Referring now to FIG. 1, a first preferred embodiment of the novel hip stem prosthesis of this invention is shown generally at 10 and includes a stem 12, a neck 14, and a bolt 16 for securely joining neck 14 to stem 12 as will be discussed more fully hereinafter. Stem 12 includes a straight, cylindrical shaft 18 having a truncated, enlarged shoulder or collar 20 at the proximal end and a plurality of longitudinal flutes 22 at the distal end. A coronal slot 24 in distal end of shaft 18 provides a limited degree of resilience to distal end of shaft 18 so that translational forces imposed thereon are more uniformly distributed to the adjacent bone (not shown).

Shoulder 20 is configured with a generally ellipsoidal profile so as to conform to the triangular segment or flare at the top of the medullary shaft (not shown). The ellipsoidal profile extends between a diametrally enlarged portion 26 surrounding a bore 30 having a bevel 31 and being formed coaxial with shaft 18 and diametrally reduced portion 28 offset from the axis of hip stem 12. The size and shape of shoulder 20 is specifically designed to conform with the cancellous bone at the proximal end of the femur (not shown). Specifically, portion 28 of shoulder 20 is designed to engage the section cut out by the calcar miller (not shown) so as to more securely engage hip stem 12 in the proximal end of the femoral canal in proximity to the cortical bone (not shown). Shoulder 20 is tapered toward the distal end of shaft 18 with a series of terrace-like surfaces 32 that form a series of transverse, right angle ridges around the body of shoulder 20 and orthogonal to the axis of shaft 18 of hip stem 12. Shoulder 20 includes a threaded bore 21 which provides for the threaded engagement of a removal tool (not shown) in the event it becomes necessary to remove hip stem 12 from the femoral canal.

Neck 14 includes an axle 40 having tapered section 44 with a cylindrical shaft 42 extending from the end of tapered section 44. Tapered section 44 is configured with about a three degree taper which is referred to in the art as a Morse taper and is designed to engage a corresponding taper in tapered bore 30 (see also FIGS. 2 and 3) in the proximal end of hip stem 12. Shaft 42 is cylindrical and dimensionally corresponds with straight bore 62 (FIG. 2). Axle 40 includes a throughbore 46 and a countersink 47 for receiving bolt 16 to securely lock neck 14 to hip stem 12. The relationship between neck 14 and hip stem 12 will be discussed more fully hereinafter with respect to the features shown in FIGS. 2–4.

Neck 14 includes an angularly offset side arm 50 which terminates in a truncated, tapered column 52 which serves as a mounting means for a hip ball (not shown). An undercut 54 adjacent the base of the column 52 is provided on each side of column 52 to accommodate engagement of a ball removal tool (not shown) when it is necessary to disassemble modular hip prosthesis 10 during repair or revision. Advantageously, neck 14 is selectively configured with a wide variety of lengths and angular orientations with respect to side arm 50 and column 52 to thereby provide the surgeon with a wide selection of hip stem configurations to meet almost every conceivable anatomical condition encountered during the surgical procedure. Importantly, the dimensional characteristics of shaft 42 and tapered section 44 are maintained with consistent and accurate dimensions so that each configuration of neck 14 will matingly engage hip stem 12.

Referring now more particularly to FIGS. 2 and 3, cross sectional views of hip stem 12 and neck 14, respectively, are shown to more clearly illustrate the internal relationship between hip stem 12 and axle 40 and, more particularly, with shaft 42 and tapered section 44 of axle 40. Shaft 42 is received in close fitting, sliding relationship in bore 62 and is designed to stabilize and support the fit between axle 40 in bore 30. Tapered section 44 is matingly received in a dimensionally corresponding tapered bore 64, the taper providing the well-known feature of a press-lock interrelationship between these two elements. However, prior to the press-lock relationship being established the angular orientation of neck 14 to collar 20 (as shown by FIG. 4) is established so as to present column 52 at the desired position to receive thereon the conventional hip ball (not shown). Thereafter, bolt 16 (FIG. 1) is inserted through throughbore 46 into threaded engagement by threads 17 on bolt 16 with threads 67. Bolt 16 is then tightened to securely engage neck 14 to hip stem 12. Bolt 16 has a countersunk head 15 that is received in countersink 47 in the proximal end of throughbore 46.

Importantly, the size and dimensional configuration including angular relation between side arm 50 and the longitudinal axis of hip stem 12 is selectively predetermined during the surgical procedure and can even be accomplished after hip stem 12 has been implanted in the final position in the femoral canal (not shown). Referring now specifically to FIG. 4, with hip stem 12 securely positioned in the femoral canal (not shown) the surgeon is able to select the appropriate configuration for neck 14 to meet the surgical conditions encountered. Neck 14 is engaged to hip stem 12 and the final angular orientation between neck 14 and hip stem 12 is established, as illustrated by the angular offset between the plane of neck 14 and the longitudinal axis of shoulder 20. Bolt 16 is used to secure the engagement between neck 14 and hip stem 12 to completely eliminate any accidental relative displacement between these two elements. In this manner the surgeon (not shown) is able to selectively obtain the best possible fit of hip stem prosthesis 10 to match the conditions encountered during the surgical procedure.

Figure 5:
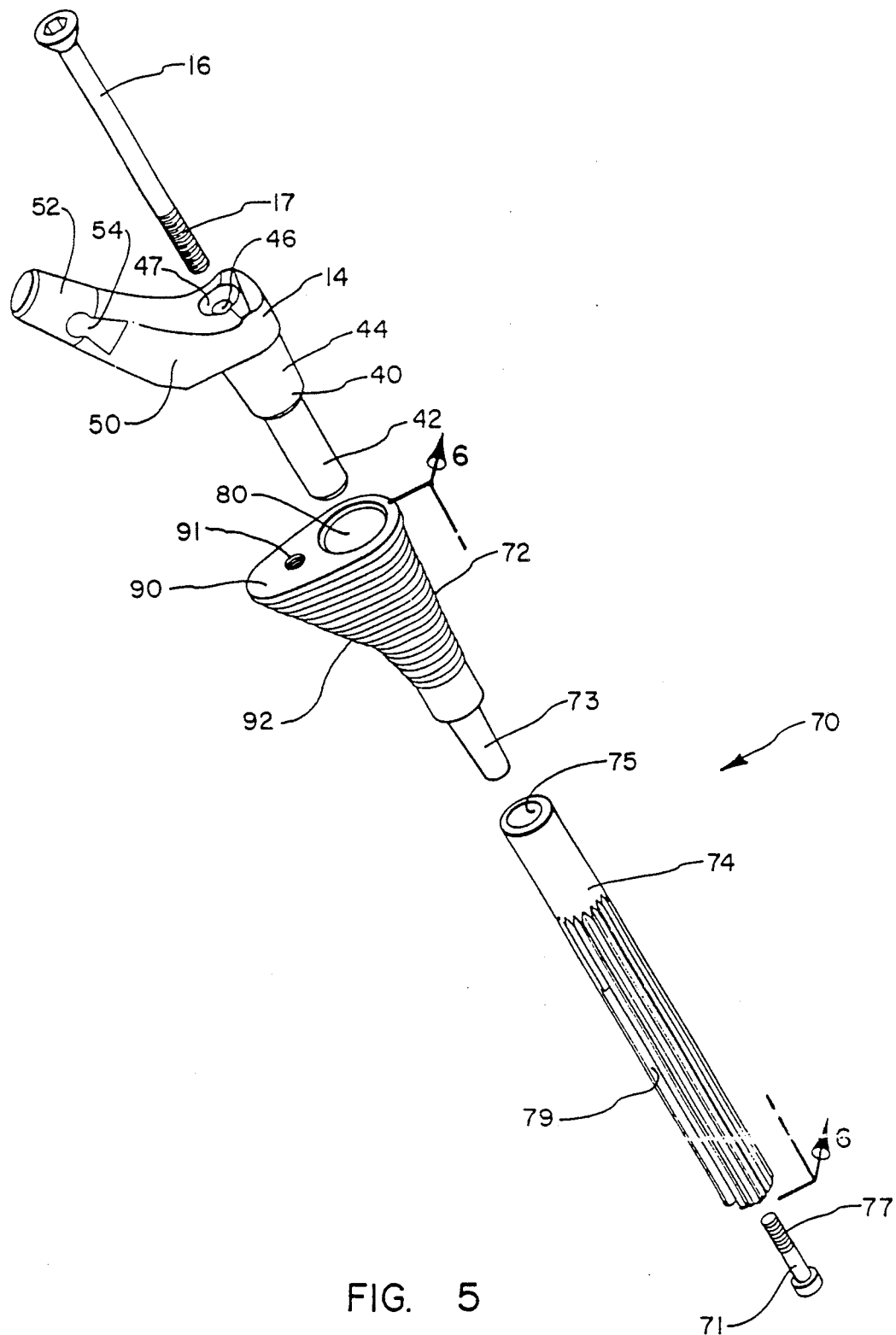
FIG. 5 is an exploded, perspective view of a second preferred embodiment of the novel hip stem prosthesis of this invention.
Figure 6:
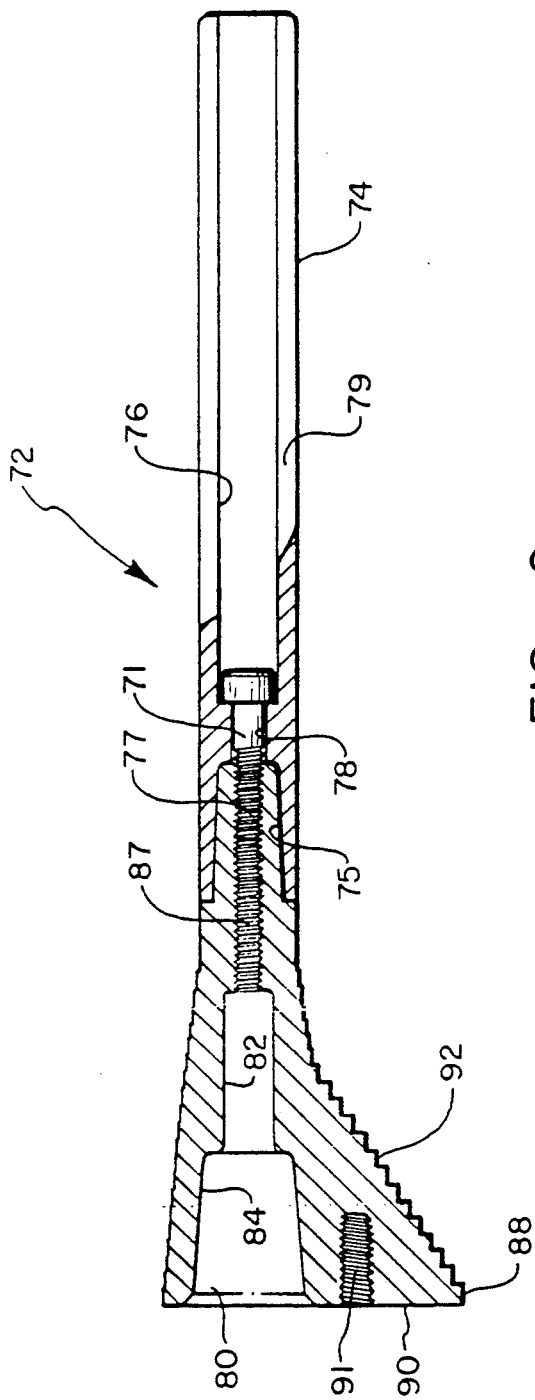
FIG. 6 is a cross sectional view of the stem portion of the second preferred embodiment of the hip stem prosthesis of this invention taken along lines 6—6 of FIG. 5 and shown in the assembled configuration.

Referring now to FIGS. 5 and 6, a second preferred embodiment of the novel hip stem prosthesis of this invention is shown generally at 70 and includes a hip stem 72 configured from a shoulder portion 90 and a distal stem portion 74. Shoulder portion 90 is configured essentially identical to shoulder 20 (FIGS. 1, 3 and 4) in that it includes a tapered section 92 having a generally ellipsoidal profile with a series of orthogonal terraces thereon for providing a close fit between shoulder 90 and the adjacent cortical bone (not shown). A tapered shaft 73 at the distal end of shoulder portion 90 is dimensionally configured to be received in press fit relationship in a tapered bore 75 in distal stem portion 74. Interiorly, tapered shaft 73 has a threaded throughbore 87 which is coaxial with a cylindrical bore 82 and a tapered bore 84. A threaded bore 91 is also provided in shoulder portion 90 for the purpose of threadedly engaging a removal tool (not shown) to shoulder portion 90 in the event it becomes necessary to remove the same.

Distal stem portion 74 includes a coronal slot 79 and a hollow bore 76 extending a substantial portion of the length of distal stem portion 74. A diametrically reduced, coaxial throughbore 78 interconnects hollow bore 76 and tapered bore 75. Throughbore 78 receives a bolt 71 so that threads 77 on bolt 71 can be threadedly engaged in threaded throughbore 87 when shoulder portion 90 is engaged to distal stem portion 74. In particular, tapered shaft 73 is inserted in tapered bore 75 in press fit relationship and secured thereto by the use of bolt 71. When thus completed, this second preferred embodiment of the hip stem of this invention, hip stem 70, is essentially identical to hip stem 13 (FIGS. 1, 2 and 4). The basic difference is that the surgeon (not shown) has available a plurality of size combinations between shoulder portion 90 and distal stem portion 74 thereby greatly increasing the ability to more closely approximate the fit between hip stem prosthesis 70 and the specific requirements of the patient (not shown).

As shown in FIG. 5, neck 14 is identical to that shown in FIGS. 1, 3 and 4 so that the various elements thereof need not be described again. Axle 40 is telescopically received in bore 80 with shaft 42 being received in bore 82 and tapered section 44 into press fit relationship in tapered bore 84. Thereafter, bolt 16 is passed through, throughbore 46 into threaded engagement with threaded bore 87. Importantly, the respective lengths of bolt 16 and bolt 71 are carefully coordinated so that each can be tightened independently without interfering with the other. Thus, both neck 14 and distal stem portion 74 are bolted into shoulder portion 90 by means of the use of a common threaded bore, threaded throughbore 87.

THE METHOD

With reference to FIGS. 1-4, the novel method of this invention is practiced by following conventional surgical techniques to secure hip stem 12 in the femoral canal. The size relationship between distal end 18 of hip stem 12 and collar 20 is determined by the surgeon (not shown) during the surgical procedure. It is almost universally accepted that initial stability of hip stem prosthesis 10 is essential in order for an uncemented total hip replacement to be successful. Stability is achieved by obtaining the appropriate degree of fill which means that the particular implant is carefully selected so as to more closely approximate the endosteal cortex in both the diaphyseal (distal) and metaphyseal (proximal) regions. The reason is that the strength of the intra medullary bone increases with the proximity to the endosteal cortex.

The diameter of distal stem 18 is determined by reaming to remove a certain amount of the endosteal cortex. Coronal slot 24 imparts a limited degree of lateral compressibility to distal stem 18 to reduce the risk of splitting the femur when the distal stem is inserted into the intramedullary canal created by the reaming procedure. As weight is applied to the femur, the femur tends to flex in the direction of the anterior bow and coronal slot 24 decreases the bending stiffness of distal stem 18 thereby reducing, if not eliminating, a specific pain referred to in the literature as thigh pain. Further, unless distal stem 18 is resiliently forced into the intramedullary canal to impose a flexure on coronal slot 24, hip stem prosthesis 10 tends to develop a toggle action during ambulatory movement by the patient.

Flutes 22 impart rotary stability to distal stem 18 since the rotary forces on hip stem prosthesis 10 are quite high. Driving distal stem 18 into the appropriately sized femoral canal forces flutes 22 into engagement with the surrounding intra medullary bone creating essential securement of distal stem 18 against rotation. This driving action also incrementally compresses coronal slot 24 so that the ends of distal stem 18 are resiliently urged outwardly into contact with the surrounding bone (not shown). Accordingly, hip stem 12 is securely engaged with adequate distal stability without further distal fixation such as by cementation.

It is well known that the metaphyseal geometry does not necessarily have any relationship to the diaphyseal geometry. Accordingly hip stem 12 is provided with a plurality of sizes for distal stem 18 and a plurality of sizes for collar 20 so as to accommodate the differences in size requirements that may be encountered. Advantageously, the total number of component parts required to be available is not that great, and the specific size relationships between distal stem 18 and collar 20 are coordinated with the particular calcar reamer so that it is a simple procedure to insert the appropriately sized hip stem 12 as predetermined by the specific calcar reamer (not shown).

Neck 14 is then selected from a plurality of configurations so as to complete the hip stem prosthesis 10 of this invention and is mounted to hip stem 12. The taper lock provided by tapered section 44 mating with tapered bore 64 has been used in orthopedic surgery for a long time. When impacted, the lock achieved is very good, and failure by disassembly in service has yet to be described in the literature. Neck 14 is further secured in the proximal end of hip stem 12 by being bolted thereto by bolt 16.

Advantageously, the method of the present invention easily accommodates disassembly of neck 14 from hip stem 12 by simply removing bolt 16 and pulling neck 14 from hip stem 12. Importantly, it is no longer necessary to also remove hip stem 12 if only neck 14 requires replacement thereby substantially reducing the risk of subsequent loss of stability if hip stem 12 were replaced.

Referring now specifically to FIGS. 5 and 6, improved selection in the various components of hip stem prosthesis 70 is provided by having hip stem 72 available as two modular components, shoulder portion 90 and distal end portion 74. Importantly, tapered shaft 73 and tapered bore 75 are dimensionally consistent regardless of the overall dimensions of the particular modular component so that each part universally fits with the other part. The advantage of this feature is readily apparent to a skilled surgeon since any suitable size distal stem portion 74 can be fitted with an appropriately dimensioned shoulder portion 90 during the surgical procedure. This is particularly advantageous for those surgical procedures where unusual conditions are abnormalities are encountered. To accomplish the foregoing, the surgeon prepares the femur according to standard surgical procedures and then selects the appropriate distal stem portion 74 and shoulder portion 90.

The orientation of shoulder portion 90 relative to coronal slot 79 is adjusted as tapered shaft 73 is joined to tapered bore 75. After a final examination for the appropriate relative orientation of these two elements, bolt 71 is passed through bores 76 and 78 into threaded engagement between threads 77 and threaded throughbore 87. Bolt 71 is then tightened so as to securely join distal stem portion 74 to shoulder portion 90 thereby providing a completed hip stem 72. Hip stem 72 is implanted in the intramedullary or femoral canal prior to neck 14 being mounted thereto as has been described in greater detail hereinbefore.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A modular hip stem prosthesis comprising:
   a hip stem comprising a distal portion having a first end and a second end, said first end comprising longitudinal flutes along an incremental length of the distal shaft and a coronal slot, said second end having an outwardly extending shoulder, said shoulder comprising a partial, first circular profile concentric with the axis of said distal shaft and extending to a second, partial circular profile offset from said first circular profile, the center of said second circular profile lying in a plane with said coronal slot, said shoulder tapering distally toward said distal shaft in a taper comprising a plurality of terraces oriented orthogonal to said axis of said distal shaft, said hip stem including an axial bore in said second end and extending through said shoulder, said bore including a cylindrical section and an outwardly flaring tapered section, and
   a neck comprising a shaft having a cylindrical section and a tapered section, said shaft being dimensionally configured to be telescopically received in said bore with said shaft cylindrical section being received slidingly in said bore cylindrical section in close fit relationship and said shaft tapered section being received in said bore tapered section in locking relationship.

2. The modular hip stem prosthesis defined in claim 1 wherein said axial bore includes a threaded bore and said neck includes an axial throughbore, said hip stem prosthesis further including a first bolt dimensionally configured to pass through said axial throughbore in said neck and into threaded engagement with said threaded bore to securely mount said neck to said hip stem.

3. The modular hip stem prosthesis defined in claim 1 wherein said second end with said shoulder is configured as a separate element having a coaxial, tapered shaft and said first end has a coaxial, tapered bore dimensionally configured to telescopically receive said tapered shaft in press fit relationship.

4. The modular hip stem prosthesis defined in claim 3 wherein said shoulder and said coaxial, tapered shaft includes a coaxial, threaded throughbore and said first end includes a coaxial bore an incremental length from said distal end and a diametrally reduced throughbore extending coaxially the rest of the length of said first end into said tapered bore, and a second bolt for passing through said coaxial bore and said diametrally reduced throughbore into threaded engagement with said threaded throughbore.

5. The modular hip stem prosthesis defined in claim 4 wherein the length of said second bolt is dimensionally coordinated with the length of said first bolt so that said first bolt and said second bolt do not interfere in said threaded throughbore.

6. A modular hip stem prosthesis comprising:
   a distal stem comprising a cylindrical shaft having a plurality of longitudinal flutes along an incremental length of the distal end and a coronal slot;
   a diametrally enlarged shoulder formed at the proximal end of the distal stem, said shoulder having a generally ellipsoidal cross section offset from the axis of said distal stem, said shoulder tapering toward the distal end of said distal stem in a plurality of terraces oriented orthogonal to said distal stem;
   a first coaxial bore in said distal stem at said proximal end, said first coaxial bore having a tapered bore terminating in a cylindrical bore, said cylindrical bore terminating in a threaded bore;
   a neck having a truncated conical section for demountably receiving a ball and an axle adapted to be telescopically received in said first coaxial bore, said axle having a coaxial throughbore and a tapered shaft dimensionally configured to be received in press fit relationship in said tapered bore and a cylindrical shaft dimensionally configured to be telescopically received in said cylindrical section in sliding relationship; and
   a bolt for passing through said coaxial throughbore into threaded engagement in said threaded bore.

7. The modular hip stem prosthesis defined in claim 6 wherein diametrally enlarged shoulder includes mounting means for demountably attaching said diametrally enlarged shoulder to said cylindrical shaft.

8. A method for providing a hip stem prosthesis comprising:
   preparing a hip stem by forming a distal shaft with a cylindrical cross section and a plurality of longitudinal flutes along a portion of the length of said distal shaft, said distal shaft including a coronal slot at said first end, an eccentric, truncated shoulder at a second end of said distal shaft, said shoulder being configured as a cylindrical shape intersecting the axis of the distal shaft to provide an eccentric, truncated profile to said shoulder;
   forming an axial bore in said second end of said distal shaft, said bore having a first, tapered section and a second, cylindrical section; and
   obtaining a neck for mounting to said hip stem by preparing a shaft on said neck, said shaft having a distal, cylindrical portion and a tapered portion, said distal, cylindrical portion being telescopically received in mating relationship with said cylindrical section of said bore, said tapered portion of said shaft mating in press-fit relationship in said tapered section of said bore in said hip stem.

9. The method defined in claim 8 wherein said obtaining step includes mounting said neck to said hip stem while selectively orienting said neck to said hip stem.

10. The method defined in claim 8 wherein said forming step includes preparing an axial, threaded bore in the end of said bore and forming an axial throughbore through said shaft, said obtaining step including selecting a threaded bolt for passing through said throughbore into threaded engagement with said threaded bore thereby securely mounting said neck to said hip stem.

11. The method defined in claim 8 wherein said preparing step includes fabricating said distal shaft as a first, separate element and said shoulder as a second, separate element and forming mating means on said first, separate element and said second, separate element for matingly joining said first, separate element to said second, separate element thereby creating said hip stem.

* * * * *